US012582469B2

(12) United States Patent (10) Patent No.: US 12,582,469 B2
Carr et al. (45) Date of Patent: Mar. 24, 2026

(54) GROUPED PIN RECEPTACLE CONNECTOR FOR ABLATION CATHETER HANDLE

(71) Applicant: Medtronic, Inc., Minneapolis, MN (US)

(72) Inventors: Julia M. Carr, Minneapolis, MN (US); Angela N. Burgess, Plymouth, MN (US); Benjamin J. Steger, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 313 days.

(21) Appl. No.: 18/360,584

(22) Filed: Jul. 27, 2023

(65) Prior Publication Data

US 2024/0032996 A1 Feb. 1, 2024

Related U.S. Application Data

(60) Provisional application No. 63/369,822, filed on Jul. 29, 2022.

(51) Int. Cl.
| *A61B 18/14* | (2006.01) |
| *A61B 18/00* | (2006.01) |
| *H01R 13/405* | (2006.01) |

(52) U.S. Cl.
CPC ....... *A61B 18/1492* (2013.01); *H01R 13/405* (2013.01); *A61B 2018/00178* (2013.01); *H01R 2201/12* (2013.01)

(58) Field of Classification Search
CPC ...... A61B 18/1492; A61B 2018/00178; A61B 2018/0091; H01R 13/405; H01R 2201/12
USPC .......................................... 606/41
See application file for complete search history.

(56) References Cited

U.S. PATENT DOCUMENTS

| 6,348,035 B1 | 2/2002 | Takami |
| 2012/0202388 A1* | 8/2012 | Selig ...................... A61B 18/14 |
| | | 439/656 |
| 2012/0283720 A1 | 11/2012 | Newton et al. |
| 2018/0132924 A1* | 5/2018 | Hermann Fakler ......................... |
| | | A61B 18/1442 |
| 2018/0221079 A1 | 8/2018 | Cohen |
| 2019/0083187 A1* | 3/2019 | Danitz ................... A61B 34/37 |
| 2019/0245310 A1* | 8/2019 | Medina .................. H01R 27/02 |
| 2019/0350638 A1 | 11/2019 | Smith et al. |
| 2020/0008865 A1 | 1/2020 | Sigmon, Jr. et al. |
| 2020/0093566 A1 | 3/2020 | Cadwell et al. |
| 2021/0022792 A1 | 1/2021 | Beaupre et al. |
| 2021/0393318 A1 | 12/2021 | Williams et al. |
| 2022/0368054 A1* | 11/2022 | Hasan ................... H01R 13/26 |

* cited by examiner

FOREIGN PATENT DOCUMENTS

| CN | 102223912 A | 10/2011 |
| WO | WO-2021173453 A1 * | 9/2021 ........... A61B 18/042 |
| WO | WO-2022098563 A1 * | 5/2022 ......... A61B 18/1492 |

*Primary Examiner* — Beverly M Flanagan
(74) *Attorney, Agent, or Firm* — Shumaker & Sieffert, P.A.

(57) ABSTRACT

An example receptacle connector for a catheter for performing pulsed field ablation (PFA). The receptacle connector includes a first side to receive electrical signals; a second side, opposite to the first side, to transfer the electrical signals to a plurality of electrodes; a surface on the first side; and a plurality of groups of pins extending from the surface. Each of the groups of pins includes at least one pin to electrically connect to a power source to receive the electrical signals, and an interlocking wall surrounding the at least one pin.

21 Claims, 8 Drawing Sheets

100

101

103

104

116

102

GROUPED PIN RECEPTACLE CONNECTOR FOR ABLATION CATHETER HANDLE

The application claims the benefit of U.S. Provisional Patent Application No. 63/369,822, filed 29 Jul. 2022, the entire contents of which is incorporated herein by reference.

TECHNICAL FIELD

The present technology is related to ablation catheters. In particular, various examples of the present technology are related to ablation catheters for performing pulse field ablation (PFA).

BACKGROUND

Tissue ablation is a medical procedure commonly used to treat conditions such as cardiac arrhythmia, which includes atrial fibrillation. For treating cardiac arrhythmia, ablation can be performed to modify tissue, such as to stop aberrant electrical propagation and/or disrupt aberrant electrical conduction through cardiac tissue. Although thermal ablation techniques are frequently used, such as cryoablation and radiofrequency (RF) ablation, non-thermal techniques such as pulsed field ablation (PFA) may also be used.

An ablation catheter may include a receptacle connector connected, by a cable, to a console having electronic components that generate electrical signals. The console may generate electrical signals, such as PFA signals, to be carried to a receptacle connector in a handle of the ablation catheter via the cable, and then to be carried to electrodes at an end of the ablation catheter to perform an electroporation procedure on tissue, such as cardiac tissue.

SUMMARY

The present technology is directed to devices, systems, and methods for performing pulsed field ablation (PFA) using a catheter. An ablation catheter may include a receptacle connector connected, such as by a cable, to a console having electronic components that generate electrical signals. The console may generate electrical signals, such as PFA signals, to be carried to a receptacle connector in a handle of the ablation catheter via the cable, and then to be carried to electrodes at an end of the ablation catheter to perform an electroporation procedure on tissue, such as cardiac tissue.

In accordance with one or more aspects of this disclosure, a receptacle connector may include a first side to receive electrical signals; a second side, opposite to the first side, to transfer the electrical signals to a plurality of electrodes; a surface on the first side; and a plurality of groups of pins extending from the surface, each of the groups of pins including: at least one pin to electrically connect to a power source to receive the electrical signals, and an interlocking wall surrounding the at least one pin.

In another example, a method for performing pulse field ablation (PFA) includes determining, by a controller connected to a catheter and at a first time, to perform PFA; responsive to determining to perform PFA, outputting, by the controller and through a receptacle connector to a plurality of electrodes of the catheter to cause the plurality of electrodes to generate a field, electrical energy to activate at least one pin in a first group of pins of a plurality of groups of pins extending from a surface of the receptacle connector.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
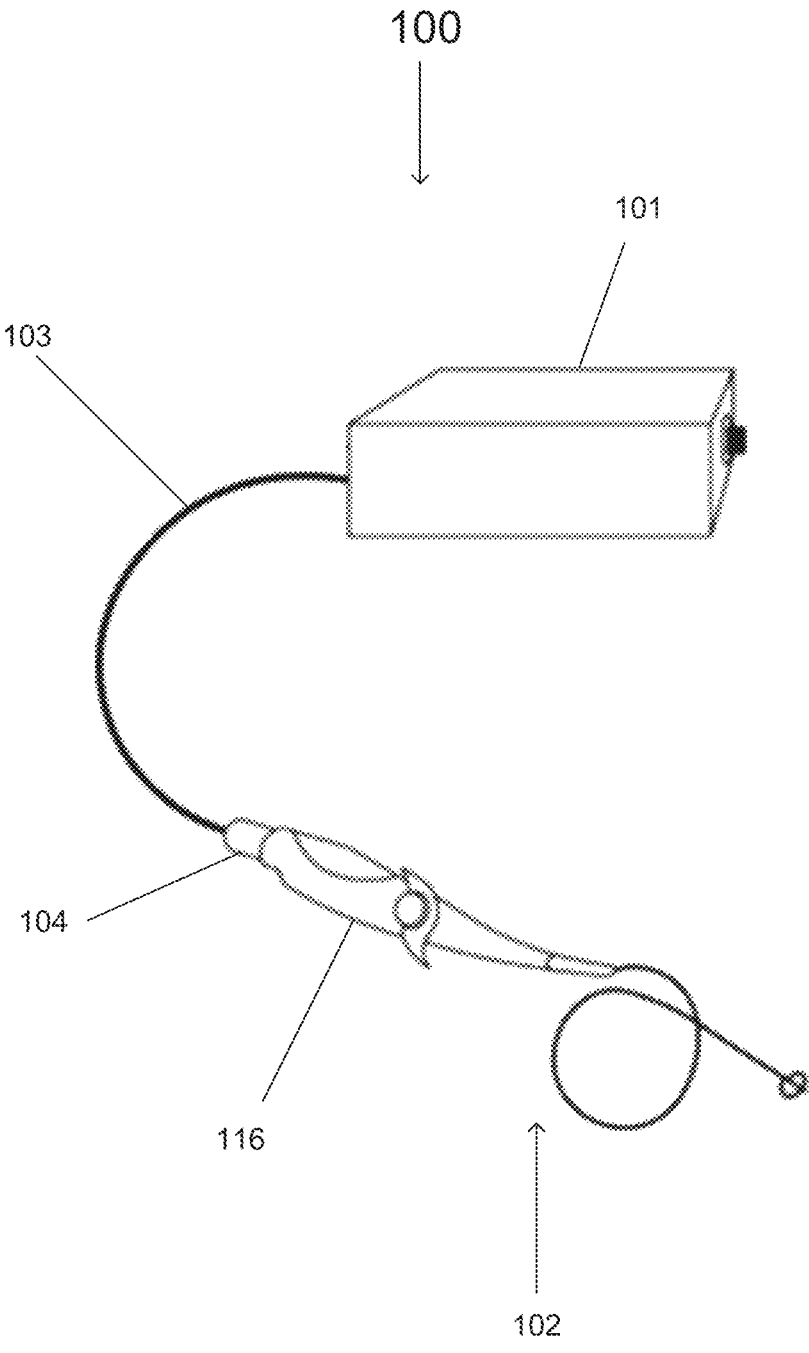
FIGS. 1A and 1B are conceptual diagrams illustrating an example system for delivering PFA, in accordance with one or more aspects of this disclosure.
Figure 1B:
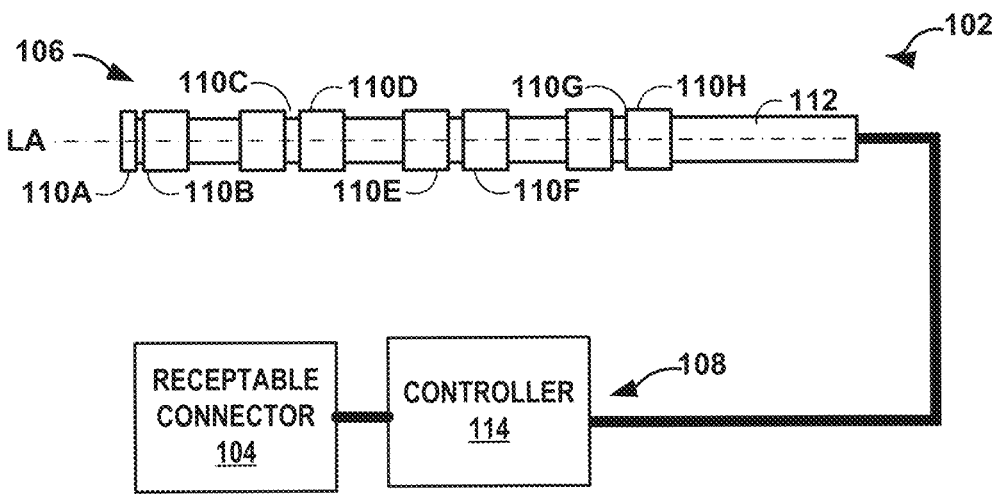

FIG. 1A is a conceptual diagram illustrating an example system 100 for delivering pulsed field ablation (PFA) that includes power source 101, catheter 102, cable 103 and receptacle connector 104. FIG. 1B is a conceptual diagram illustrating part of example system 100 that includes catheter 102, receptacle connector 104, and controller 114. Catheter 102 may include elongated structure 112 carrying a plurality of electrodes 110A-110H (collectively, "electrodes 110").

In general, to deliver PFA, a practitioner (e.g., cardiologist, surgeon, etc.) may insert catheter 102 into a patient and cause power source 101 to deliver, via cable 103, receptacle connector 104, and catheter 102, electroporation energy (e.g., pulsed field ablation energy). Electroporation may be a phenomenon causing cell membranes to become "leaky" (that is, permeable for molecules for which the cell membrane may otherwise be impermeable or semipermeable). Electroporation, which may also be referred to as electropermeabilization, pulsed electric field treatment, non-thermal irreversible electroporation, irreversible electroporation, high frequency irreversible electroporation, nanosecond electroporation, or nanoelectroporation, may involve the application of high-amplitude pulses to cause physiological modification (i.e., permeabilization) of the cells of the tissue to which the energy is applied. These pulses may be short (for example, nanosecond, microsecond, or millisecond pulse width) in order to allow the application of high voltage, high current (for example, 20 or more amps) without long duration(s) of electrical current flow that may otherwise cause significant tissue heating and muscle stimulation. The pulsed electric energy may induce the formation of microscopic defects that result in hyperpermeabilization of the cell membrane. Depending on the characteristics of the electrical pulses, an electroporated cell can survive electroporation, referred to as "reversible electroporation," or die, referred to as "irreversible electroporation" (IRE).

Reversible electroporation may be used to transfer agents, including genetic material and other large or small molecules, into targeted cells for various purposes, including the alteration of the action potentials of cardiac myocytes.

In some examples, the examples of receptacle connectors, as discussed in this disclosure, may improve usability of system 100 to deliver PFA while maintaining a size and weight of catheter 102 below a threshold. In some examples, as discussed in this disclosure, a receptable connector having a plurality of groups of pins, in which the pin(s) in each group of pins may be arranged in the receptable connector and surrounded by a respective interlocking wall, to separate the groups of pins, may help receptable connector meet the electrical creepage and clearance requirements while keeping a size of the receptable connector small enough to fit at least partially within the handle of catheter.

Power source 101 may include an energy generator configured to provide electrical pulses to electrodes 110 via cable 103 and receptacle connector 104 to perform an electroporation procedure to cardiac tissue or other tissues within the patient's body, such as renal tissue, airway tissue, and organs or tissue within the cardiac space or the pericardial space. For instance, the energy generator may be configured and programmed to deliver pulsed, high-voltage electric fields appropriate for achieving desired pulsed, high-voltage ablation (referred to as "pulsed field ablation" or "pulsed electric field ablation") and/or pulsed radiofrequency ablation. As a point of reference, the non-radiofrequency pulsed high-voltage ablation effects of the present disclosure are distinguishable from DC current ablation, as well as thermally-induced ablation attendant with conventional RF techniques. For example, the pulse trains delivered by the energy generator may be delivered at a frequency less than 30 kHz, and in an example configuration, 1 kHz, which is a lower frequency than radiofrequency treatments. The pulsed-field energy in accordance with the present disclosure may be sufficient to induce cell death for purposes of completely blocking an aberrant conductive pathway along or through cardiac tissue, destroying the ability of the so-ablated cardiac tissue to propagate or conduct cardiac depolarization waveforms and associated electrical signals. Additionally or alternatively, the energy generator may be configured and programmed to deliver RF energy appropriate for achieving tissue ablation.

In some examples, cable 103 may electrically connect power source 101 and catheter 102. A connection point for the cable 103 and catheter 102 may include receptacle connector 104. In some examples, receptacle connector 104 may be located at a handle of catheter 102 and is positioned at least partially inside an exterior shell of the handle of catheter 102. Receptacle connector 104 may include a plurality of electrical connectors, such as pins (not shown in FIGS. 1A, 1B). In some examples, electrical connectors may connect different electronic devices so electrical signals may be transmitted and/or electrical power may be distributed between different electronic devices. Electrical connectors may include board-to-board connectors, wire/cable-to-wire/cable connectors, or wire/cable-to-board connectors.

In some examples, according to aspects of this disclosure, receptacle connector 104 may be configured to have a small enough size to fit at least partially within the handle of catheter 102 and include a plurality of groups of pins arranged in a manner to meet the electrical creepage and clearance requirements for a selected voltage therapy. In some examples, receptacle connector 104 may be configured to fit at least partially within the handle of catheter 102 and include a plurality of groups of pins arranged in a manner to meet the creepage and clearance requirements of 1500 voltage therapy. In some examples, as discussed in this disclosure each group of pins may be arranged in receptable connector 104 to separate the groups of pins to allow for electrical creepage and clearance requirements to be met while keeping a size of the receptable connector below a threshold. In addition, the pin(s) in each group of pins may be respectively surrounded by an interlocking wall to increase creepage distance between different groups of pins. Accordingly, one or more of the arrangement of the groups of pins in the receptable connector and/or the interlocking walls surrounding the pin(s) in each group of pins may help receptable connector 104 meet electrical creepage and clearance requirements while keeping a size of receptable connector 104 small enough to fit at least partially within the handle of catheter.

In some examples, catheter 102 may generally include features that enable insertion of catheter 102 into a patient and navigation of catheter 102 to a target treatment site. Elongated structure 112 may include a distal portion 106 and a proximal portion 108. Electrodes 110 may be generally positioned at distal portion 106, while proximal portion 108 may be connected to receptacle connector 104. Electrodes 110 may be of any suitable geometry. Example geometries of electrodes include, but are not necessarily limited to, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes). Electrodes 110 may be axially distributed along longitudinal axis LA of elongated structure 112.

Elongated structure 112 may include conductors configured to carry electrical signals between electrodes 110 and receptacle connector 104. In some examples, elongated structure 112 may include a separate conductor for each of electrodes 110. For instance, in the example of FIG. 1B where electrodes 110 includes eight electrodes, elongated structure 112 may include eight separate conductors. In this way, elongated structure may enable each electrode of electrodes 110 to be driven with a different signal. In other examples, multiple electrodes of electrodes 110 may share a common conductor. For instance, electrodes 110C and 110D may be connected to a same (e.g., a common) conductor. While such a common conductor arrangement may reduce flexibility (e.g., as electrodes connected to the common conductor may be driven with a same signal), such an arrangement may reduce manufacturing complexity and/or cost.

In some examples, controller 114 may control the electrical current and/or voltages to transfer to the electrodes 110 from the receptacle connector 104. In some examples, controller 114 may include a printed circuit board. In some examples, controller 114 may be located in handle 116 of catheter 102. In some examples, controller 114 may be located in power source 101.

In some examples, controller 114 may operate a selected mode of catheter 102. For instance, to operate catheter 102 in a focal mode, controller 114 may output energy to electrodes 110 to cause electrodes 110 to generate a field with a geometry focused at a distal portion 106 of catheter 102 (e.g., focused at tip electrode 110A). Such a focused field geometry may result in lesions forming proximal to the tip of catheter 102. To operate catheter 102 in the linear mode, controller 114 may output energy to electrodes 110 to cause electrodes 110 to generate a field with a geometry that is relatively even linearly along an active portion of catheter 102 (e.g., along a portion of catheter 102 on which electrodes 110 are positioned). Such a linear field geometry may result in lesions forming longitudinally along the active portion of catheter 102.

In the example of FIG. 1B, electrodes 110 are illustrated as has having a larger diameter than elongated structure 112. In some examples, one or more of electrodes 110 may have a diameter that is approximately equal to a diameter of elongated structure 112. For instance, electrodes 110 may be recessed in elongated structure 112 such that the combination results in a relatively smooth outer surface.

Although not shown, system 100 may include one or more sensors to monitor the operating parameters through the medical system 100, such as temperature, delivered voltage, or the like, and for measuring and monitoring one or more tissue characteristics, such as EGM waveforms, monophasic action potentials, tissue impedance, or the like, in addition to monitoring, recording, or otherwise conveying measurements or conditions within the energy delivery device or other component of system 100 or the ambient environment at the distal portion of the energy delivery device. The sensor(s) may be in communication with controller 114 for initiating or triggering one or more alerts or ablation energy delivery modifications during operation of the energy delivery device.

Figure 2:
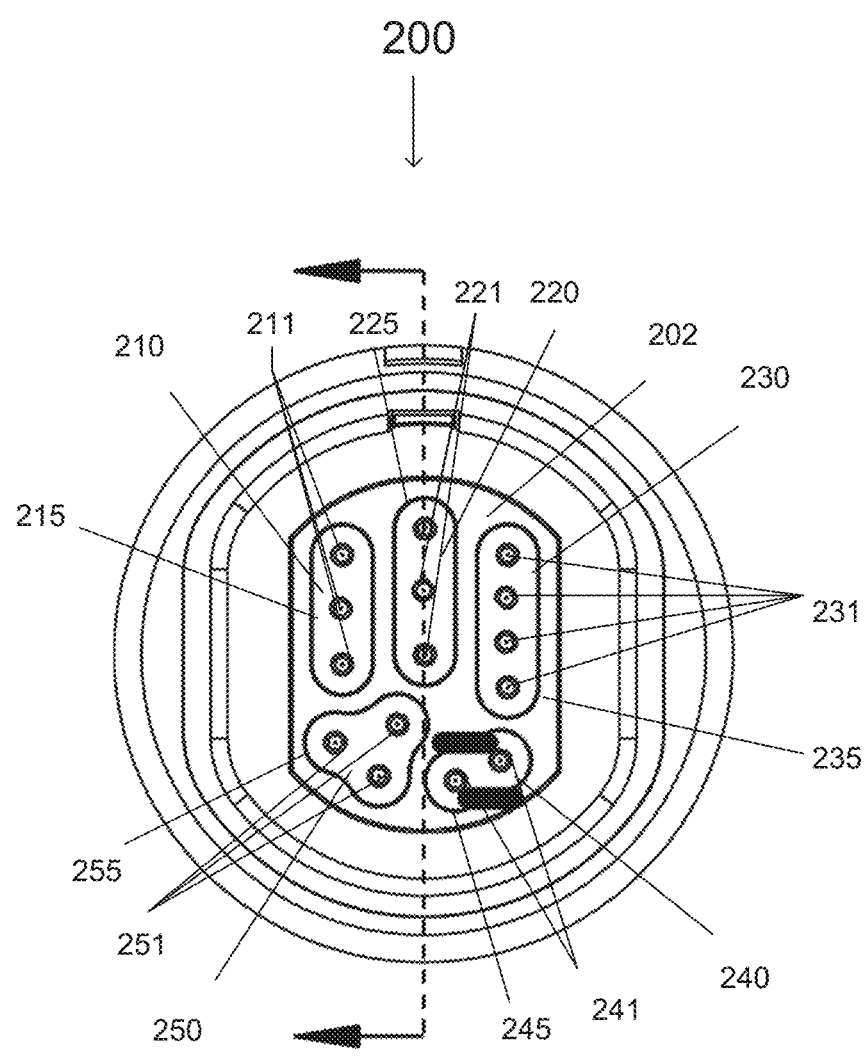
FIG. 2 is a conceptual diagram illustrating an example of a first side of receptacle connector, in accordance with one or more aspects of this disclosure.

FIG. 2 is a conceptual diagram illustrating an example of a first side of receptacle connector 200 for performing PFA, in accordance with one or more aspects of this disclosure. Receptacle connector 200 may be an example of receptacle connector 104 as shown in FIGS. 1A and 1B. The first side of receptacle connector 200 may be arranged to receive electrical signals, such as from a power source, such as power source 101 shown in FIG. 1. A second side of receptacle connector 200 (not shown in FIG. 2) may be opposite to the first side and may transfer the electrical signals to a plurality of electrodes, such as electrodes 110 shown in FIG. 1.

In some examples, a size of receptacle connector 200 may be limited to fit inside a catheter handle. In some examples, the catheter handle may be a PVAC GOLD® catheter handle. A receptacle connector may include a plurality of pins, with each pin having a creepage distance and clearance distance between each other. In some examples, pins that do not have an interlocking wall between them have low creepage and clearance distances between them. However, in some examples, while a receptacle connector with an interlocking wall between each and every pin may result in maximized electrical isolation between every pin, a receptacle connector with an interlocking pin between each and every pin may result in the receptacle connector being unable to fit inside a catheter handle, such as the PVAC GOLD® catheter handle.

In some examples, the techniques of this disclosure may help to minimize space requirements needed for relatively high-voltage connections in a catheter, such as those described herein. For example, receptacle connector 200 may include lower surface 202 and a plurality of groups 210, 220, 230, 240, 250 of pins. At least one of the groups of pins 210, 220, 230, 240, 250 may extend from lower surface 202. Receptacle connector 200 is not limited to the number of groups shown in FIG. 2 and may have more or less groups than shown in FIG. 2. Lower surface 202 may surround plurality of groups 210, 220, 230, 240, 250 of pins. In general, grouping pins in the manner described in this disclosure, may meet creepage and/or clearance distance thresholds between the respective groups of pins for receptable connector 104 to operate properly while keeping a size of receptable connector 104 small enough to fit at least partially within handle 116 of catheter 102.

In some examples, receptacle connector 200 may include a plurality of groups 210, 220, 230, 240, 250 of pins. Receptacle connector 200 is not limited to the number of groups shown in FIG. 2 and may have more or less groups than shown in FIG. 2. In some examples, first group 210 may include at least one pin 211 and interlocking wall 215. In some examples, one or more of interlocking walls 215, 225, 235, 245, 255 of a respective group of the plurality of groups 210, 220, 230, 240, 250 may comprise an insulating material. In some examples, one or more of interlocking walls 215, 225, 235, 245, 255 may extend from lower surface 202. In some examples, an interlocking wall of a respective group may surround each of the pins of the respective group. In some examples, an interlocking wall of a respective group may create an outer perimeter of the respective group. In some examples, an interlocking wall of a respective group may extend to a space surrounding one or more respective pins of the respective group. In some examples, a presence of an interlocking wall may increase creepage distance between two groups of pins that maintain the same clearance distance. In some examples, first group 210 may include at least two pins 211. First group 210 is not limited to the number of pins shown in FIG. 2 and may have more or less pins than shown in FIG. 2. In general, grouping pins with interlocking walls separating the respective groups in the manner described in this disclosure, may meet creepage and/or clearance distance thresholds between the respective groups of pins for receptable connector 104 to operate properly while keeping a size of receptable connector 104 small enough to fit at least partially within handle 116 of catheter 102.

In some examples, second group 220 may include at least one pin 221 and interlocking wall 225. In some examples, second group 220 may include at least two pins 221. Second group 220 is not limited to the number of pins shown in FIG. 2 and may have more or less pins than shown in FIG. 2. In some examples, third group 230 may include at least one pin 231 and interlocking wall 235. In some examples, third group 230 may include at least two pins 231. Third group 230 is not limited to the number of pins shown in FIG. 2 and may have more or less pins than shown in FIG. 2. In some examples, fourth group 240 may include at least one pin 241 and interlocking wall 245. In some examples, fourth group 240 may include at least two pins 241. Fourth group 240 is not limited to the number of pins shown in FIG. 2 and may have more or less pins than shown in FIG. 2. In some examples, fifth group 250 may include at least one pin 251 and interlocking wall 255. In some examples, fifth group 250 may include at least two pins 251. Fifth group 250 is not limited to the number of pins shown in FIG. 2 and may have more or less pins than shown in FIG. 2.

In some examples, pins 211, 221, 231, 241, 251 in receptacle connector 200 may refer to a variety of electrical connectors to connect different electronic devices, such as power source 101 and catheter 102, so electrical signals may be transmitted and/or electrical power may be distributed between different electronic devices. Pins 211, 221, 231, 241, 251 may include board-to-board connectors, wire/cable-to-wire/cable connectors, or wire/cable-to-board connectors. In some examples, at least one of pins 211, 221, 231, 241, 251 are to electrically connect to a power source receive electrical signals from the power source. Pins 211, 221, 231, 241, 251 may include high-voltage connector pins and/or low-voltage connector pins. In some examples, pins 211, 221, 231, 241, 251, may total 15 pins, as shown in FIG. 2. In some examples, four of 211, 221, 231, 241, 251 pins may be low-voltage connector pins while eleven of 211, 221, 231, 241, 251 pins may be high-voltage connector pins. Receptacle connector 200 may transfer the received electrical signals to be carried to electrodes at an end of catheter 102 to perform an electroporation procedure on tissue, such as cardiac tissue.

In some examples, pins of one group may electrically connect to a printed circuit board on a second side of receptacle connector 200 so the printed circuit board is in electrical communication with controller 114.

In some examples, pins of a respective group, such as pins 211 of group 210, may be grouped together so neighboring pins of the same group have electric potential differentials during a therapy mode of catheter 102 below an electrical breakdown threshold. The electrical breakdown threshold being the amount of electrical potential difference between two pins, such as two of pins 211, that may cause an electrical breakdown between the two pins.

Pins 211, 221, 231, 241, 251 are to connect with a cable connector (not shown) at an end of cable 103. In some examples, pins 211, 221, 231, 241, 251 may be male type connectors to connect with female type pins of cable connector. Pins of cable connector are to respectively correspond to pins 211, 221, 231, 241, 251 of receptacle connector 200 to electrically connect cable 103 and receptacle connector 104, 200.

In some examples, interlocking wall 215 of group 210 surrounds at least one of pins 211. In some examples, interlocking wall 215 of group 210 surrounds each of pins 211. Interlocking wall 215 extends from lower surface 202. In some examples, at least one of interlocking walls 215, 225, 235, 245, 255 extend from lower surface 202. In some examples, each of interlocking walls 215, 225, 235, 245, 255 extend from lower surface 202.

In some examples, at least two groups 210, 220 may be separated from each other by a space. In some examples, each group 210, 220, 230, 240, 250 of pins may be separated by a space from the other respective groups of pins. In some examples, a space separates at least two of interlocking walls 215, 225, 235, 245, 255. In some examples, a respective space separates each of interlocking walls 215, 225, 235, 245, 255. In some examples, at least one interlocking wall 215, 225, 235, 245, 255 may be shaped as a discorectangle.

In some examples, at least two groups 210, 220 may be separated from each other by a creepage distance, the creepage distance being greater than a creepage distance threshold. In some examples, a creepage distance threshold may be based, at least in part, to a distance between groups of pins, when a particular voltage is applied to the pins, necessary for the receptable connector to operate properly without arcing between the respective groups of pins. In some examples, a creepage distance threshold may be based on minimum spacing standards. In some examples, each group 210, 220, 230, 240, 250 of pins may be separated may be separated by a creepage distance from the respective other groups of pins, the creepage distance being greater than a creepage distance threshold. In some examples, the creepage distance threshold may correspond to a creepage requirement of 1500 volt therapy. In some examples, the creepage distance threshold may correspond to a creepage requirement of 1000 volt therapy. In some examples, the creepage distance threshold may correspond to a creepage requirement of 3000-volt therapy. The creepage requirement is not limited to the examples of creepage requirement volt therapy given above. In some examples, as voltage of volt therapy increases, the creepage distance threshold increases.

In some examples, at least two groups 210, 220 may be separated from each other by a clearance distance, the clearance distance being greater than a clearance distance threshold. In some examples, a clearance distance threshold may be based, at least in part, to a distance between groups of pins, when a particular voltage is applied to the pins, necessary for the receptable connector to operate properly without arcing between the respective groups of pins. In some examples, a clearance distance threshold may be based on minimum spacing standards. In some examples, each group 210, 220, 230, 240, 250 of pins may be separated may be separated by a clearance distance from the respective other groups of pins, the clearance distance being greater than a clearance distance threshold. In some examples, the clearance distance threshold may correspond to a clearance requirement of 1500 volt therapy. In some examples, the clearance distance threshold may correspond to a clearance requirement of 1000 volt therapy. In some examples, the clearance distance threshold may correspond to a clearance requirement of 3000-volt therapy. The clearance requirement is not limited to the examples of clearance requirement volt therapy given above. In some examples, as voltage of volt therapy increases, the clearance distance threshold increases.

In some examples, each of the pins in a respective group of pins is electrically isolated from each of the pins in a different group of pins. In an example, pins 211 in group 210 may be electrically isolated from pins 221, 231, 241, 251 respectively in groups 220, 230, 240, 250. In some examples, pins of other groups may be electrically isolated from the pins of other respective groups, such as pins 221 in group 220 may be electrically isolated from pins 211, 231, 241, 251 respectively in groups 210, 230, 240, 250.

In some examples, only one pin in a respective group of pins 211, 221, 231, 241, 251 may activate at a same time during performance of PFA. In some examples, pin 211 in first group 210 may to be driven to negative polarity and pin 221 of second group 220 may be driven to a positively polarity.

In some examples, receptacle connector 200 includes a combination of groups of pins 210, 220, 230, 240, and 250 and interlocking walls 215, 225, 235, 245, and 255 to maximize electrical isolation of groups of pins that may experience the highest electrical potential between the groups while maintaining a size of receptacle connector 200 being able to fit inside a catheter handle, such as the PVAC GOLD® catheter handle.

In accordance with one or more aspects of this disclosure, receptacle connector 200 may be configured to have a small enough size to fit at least partially within a catheter handle while meeting the electrical creepage and clearance requirements. In some examples, receptacle connector 200 may be configured to fit at least partially within the handle of the ablation catheter and include a plurality of groups of pins arranged in a manner to meet the creepage and clearance requirements of 1500 volt therapy. In an example, a clearance distance threshold may be 9 millimeters (mm) and a creepage distance threshold may be 16 mm. Accordingly, the groups of pins may be arranged in the receptable connector to meet the respective clearance distance threshold and creepage distance threshold. In some examples, interlocking wall sizes may vary to meet the respective creepage distance threshold.

Figure 3:
FIG. 3 is conceptual diagrams illustrating an example of a side view of receptacle connector, in accordance with one or more aspects of this disclosure.
Figure 3:
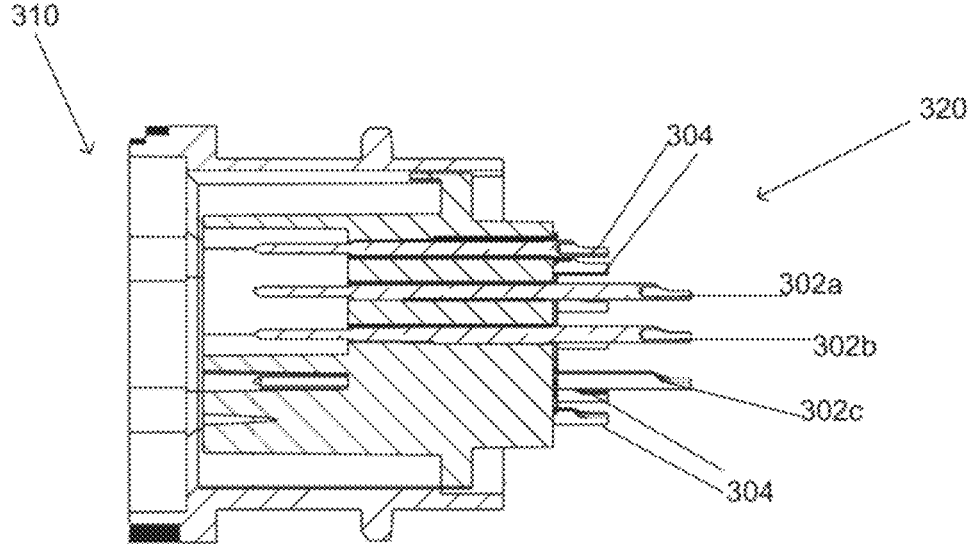

FIG. 3 is a conceptual diagram illustrating an example of a side view of receptacle connector 300 for performing PFA, in accordance with one or more aspects of this disclosure. Receptacle connector 300 of FIG. 3 may be an example of receptacle connector 104 of FIGS. 1A and 1B and/or an example of receptacle connector 200 of FIG. 2.

In some examples, the plurality of pins of a receptacle connector, such as pins 211, 221, 231, 241, 251 of receptacle connector 200 in FIG. 2 may include long pins 302 and short pins 304. In some examples, as shown in FIG. 3, two long pins 302a, 302b, may be part of group 210, and long pin 302c may be part of group 250. In this example, when two long pins 302a, 302b, may be part of group 210, and long pin 302c may be part of group 250, creepage distance between 302a, 302b and long pin 302c may be increased due to the respective interlocking walls 215 and 255 separating the long pins in comparison if no interlocking wall separated the pins.

FIG. 3 shows an example of receptacle connector 300 for performing PFA, in accordance with one or more aspects of this disclosure. First side 310 of receptacle connector 300 may be arranged to receive electrical signals, such as from a power source, such as power source 101 shown in FIG. 1. Second side 320 of receptacle connector 300 may be opposite to first side 310 and may transfer the electrical signals to a plurality of electrodes, such as electrodes 110 shown in FIG. 1.

Figure 4A:
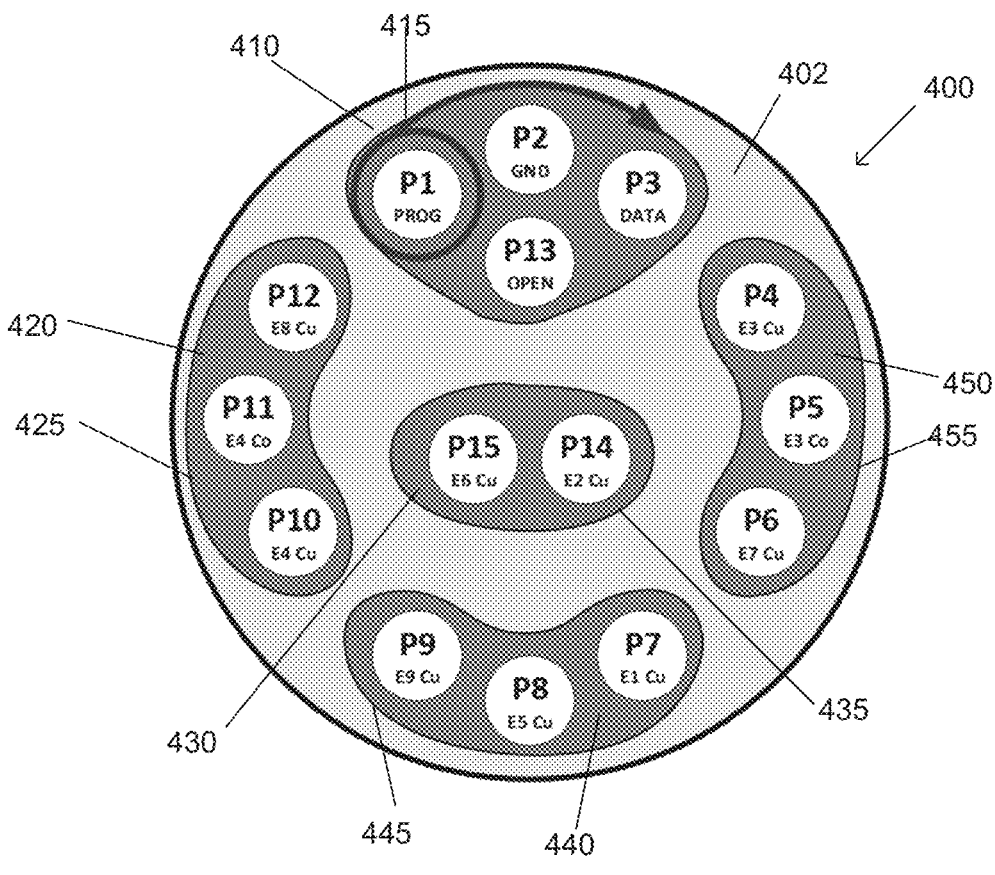
FIG. 4A is a conceptual diagram illustrating an example of a first side of receptacle connector, in accordance with one or more aspects of this disclosure.
Figure 4B:
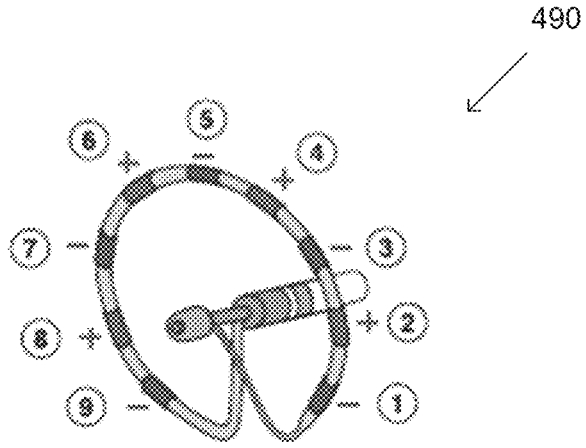
FIG. 4B is a conceptual diagram illustrating an example of an arrangement of electrodes at a distal end of a catheter.

FIG. 4A is a conceptual diagram illustrating an example of a first side of receptacle connector 400 for performing PFA, in accordance with one or more aspects of this disclosure. Receptacle connector 400 of FIG. 4A may be an example of receptacle connector 104 of FIGS. 1A and 1B. Receptacle connector 400 of FIG. 4A may be an alternative example of receptacle connector 200 of FIG. 2. FIG. 4B is a conceptual diagram illustrating an example of an arrangement of electrodes at a distal end 490 of a catheter.

In some examples, receptacle connector 400 may include lower surface 402 and a plurality of groups 410, 420, 430, 440, 450 of pins. At least one of the groups of pins 410, 420, 430, 440, 450 may extend from lower surface 402. Lower surface 402 may surround plurality of groups 410, 420, 430, 440, 450 of pins.

In some examples, receptacle connector 400 may include a plurality of groups 410, 420, 430, 440, 450 of pins. Receptacle connector 200 is not limited to the number of groups shown in FIG. 2 and may have more or less groups than shown in FIG. 2. In FIG. 4A, first group 410 includes pins P1, P2, P3, and P13 and interlocking wall 415. In FIG. 4A, second group 420 includes pins P10, P11, and P12, and interlocking wall 425. In FIG. 4A, third group 430 includes pins P14 and P15, and interlocking wall 435. In FIG. 4A, fourth group 440 includes pins P7, P8, and P9, and interlocking wall 445. In FIG. 4A, fifth group 450 includes pins P4, P5, and P6, and interlocking wall 455.

In some examples, pins P1, P2, P3, and P13 of first group 410 may electrically connect to a printed circuit board (not shown) on a second side of receptacle connector 400.

FIG. 4B shows an example of an arrangement of electrodes 1-9 at a distal end 490 of a catheter. FIG. 4B shows electrodes 1-9.

In some examples, each pin in a respective group of pins may be configured to transfer electrical energy to the same group of respective electrode(s) of the plurality of electrodes.

In some examples, pins P4, P5, and P6 of fifth group 450 may be electrically connected to electrodes 3 and 7 to transfer electrical energy to electrodes 3 and 7. Pins P7, P8, and P9 of fourth group 440 may be electrically connected to electrodes 1, 5, and 9 to transfer electrical energy to electrodes 1, 5, and 9. Pins P10, P11, and P12 of second group 420 may be electrically connected to electrodes 4 and 8 to transfer electrical energy to electrodes 4 and 8. Pins P14 and P15 of third group 430 may be electrically connected to electrodes 2 and 6 to transfer electrical energy to electrodes 2 and 6.

In some examples, each of the pins in a respective group of pins may be electrically isolated from each of the pins in a different group of pins. In some examples, each group of pins may be configured to transfer electrical energy to different respective electrode(s) than the other respective groups of pins, such as group 450 being configured to transfer electrical energy to electrodes 3 and 7, group 440 may be configured to transfer electrical energy to electrodes 1, 5, and 9, group 430 may be configured to electrodes 2 and 6, and group 420 may be configured to transfer electrical energy to electrodes 4 and 8.

In some examples, a relatively constant voltage may be applied to each of the pins in a respective group. In an example, a maximum voltage of 0 volts may be applied to the pins of fifth group 450, a maximum voltage of 0 volts may be applied to the pins of fourth group 440, a voltage maximum of 1200 volts may be applied to the pins of third group 430, and a voltage maximum of 1200 volts may be applied to the pins of second group 420. In an example, a maximum of 5 volts may be applied to the pins of the first group 410, which are connected to a printed circuit board. The voltage levels of 0, 5, and 1200 are examples and are not limited to this examples. Other voltages may also be applied to the different groups.

Figure 5:
FIG. 5 is a is a conceptual diagram illustrating an example of a catheter handle, in accordance with one or more aspects of this disclosure.
Figure 5:
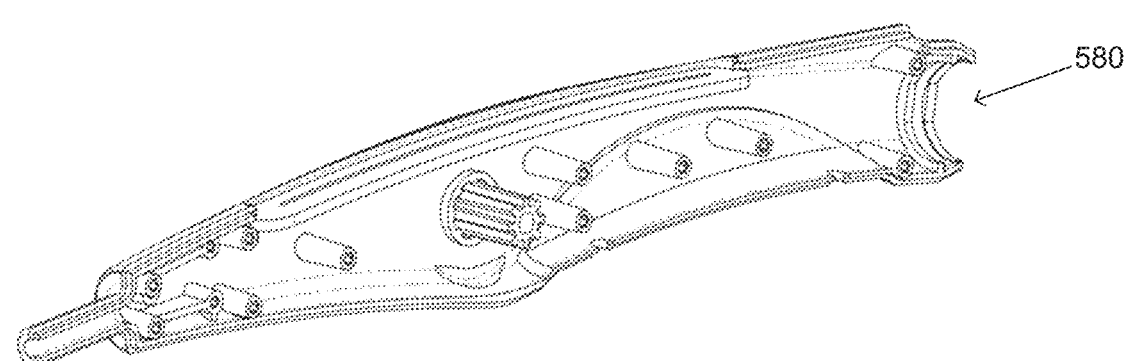

FIG. 5 is a conceptual diagram illustrating an example of a catheter handle 500 for partially holding receptacle connector, in accordance with one or more aspects of this disclosure. In some examples, a receptacle connector, such as those discussed above, are to be of a size to fit at least partially inside location 580 of catheter handle 500, such as the PVAC GOLD® catheter handle.

Figure 6:
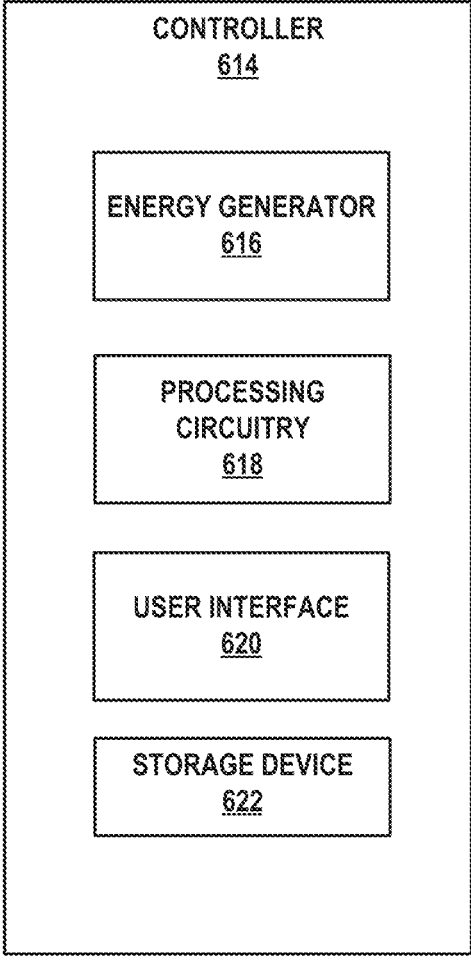
FIG. 6 is a block diagram illustrating an example controller of a system for delivering PFA, in accordance with one or more aspects of this disclosure.

FIG. 6 is a block diagram illustrating an example controller of a system for delivering PFA, in accordance with one or more aspects of this disclosure. Controller 614 of FIG. 6 may be an example of controller 114 of FIG. 1B. As shown in FIG. 6, controller 614 may include energy generator 616, processing circuitry 618, user interface 620, and storage device 622.

Energy generator 616 may be configured to provide electrical pulses to electrodes (e.g., electrodes 110 of FIG. 1) to perform an electroporation procedure to cardiac tissue or other tissues within the patient's body, such as renal tissue, airway tissue, and organs or tissue within the cardiac space or the pericardial space. For instance, energy generator 616 may be configured and programmed to deliver pulsed, high-voltage electric fields appropriate for achieving desired pulsed, high-voltage ablation (referred to as "pulsed field ablation" or "pulsed electric field ablation") and/or pulsed radiofrequency ablation. While shown in the example of FIG. 6 as a single energy generator, energy generator 616 is not so limited. For instance, controller 614 may include multiple energy generators that are each capable of generating ablation signals in parallel.

Processing circuitry 618 may include one or more processors, such as any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 618 herein may be embodied as firmware, hardware, software or any combination thereof. Processing circuitry 618 controls energy generator 616 to generate signals according to various settings. In some examples, processing circuitry 618 may execute other instructions stored in storage device 622 to perform PFA.

Storage device 622 may be configured to store information within controller 614, respectively, during operation. Storage device 622 may include a computer-readable storage medium or computer-readable storage device. In some examples, storage device 622 includes one or more of a short-term memory or a long-term memory. Storage device 622 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 622 is used to store data indicative of instructions, e.g., for execution by processing circuitry 518, respectively.

User interface 620 may include a button or keypad, lights, a speaker for voice commands, a display, such as a liquid crystal (LCD), light-emitting diode (LED), or organic light-emitting diode (OLED). In some examples, the display includes a touch screen. User interface 620 may be configured to display any information related to the performance of PFA. User interface 620 may also receive user input (e.g., selection of linear or focal PFA mode) via user interface 620. The user input may be, for example, in the form of pressing a button on a keypad or selecting an icon from a touch screen.

Figure 7:
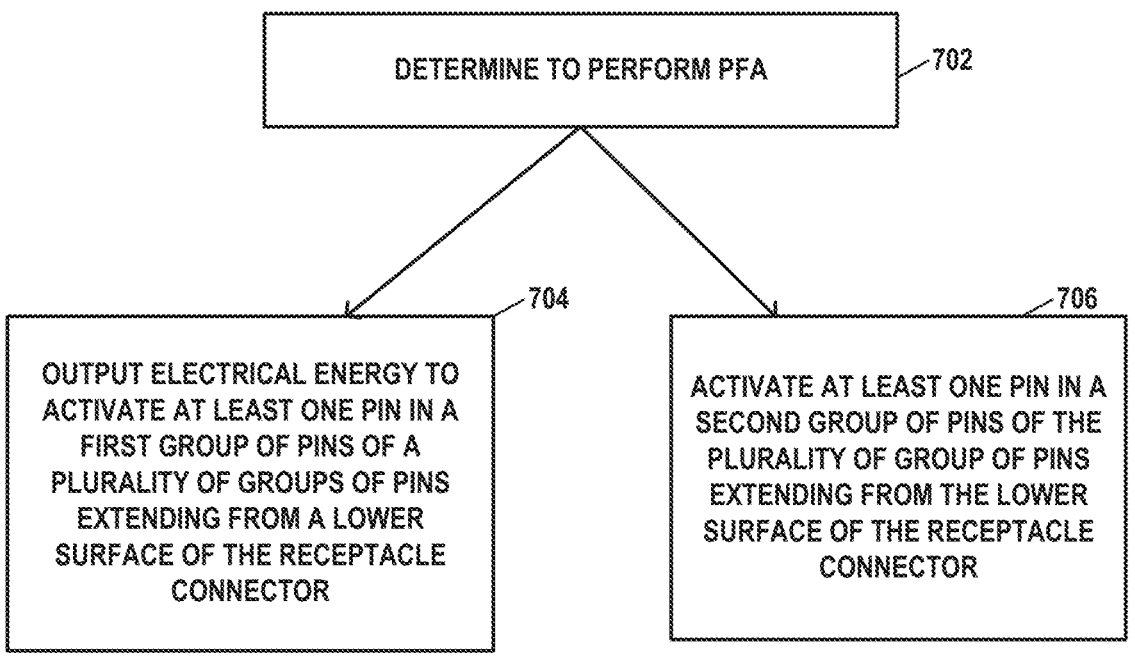
FIG. 7 is a flowchart illustrating an example technique for performing PFA, in accordance with one or more techniques of this disclosure.

FIG. 7 is a flowchart illustrating an example technique for using a single catheter to perform PFA, in accordance with one or more techniques of this disclosure. The technique of FIG. 7 may be performed by a controller, such as controller 114 of FIG. 1B or controller 614 of FIG. 6.

Controller 614 may determine to perform PFA (702). In some examples, controller 614 may determine to perform PFA based on receiving an input signal, such as from a user, for example a clinician. For instance, processing circuitry 618 of controller 614 may receive, such as via user interface 620, a selection from a practitioner whether to perform PFA.

Controller 614 may output electrical energy to activate at least one pin in a first group of pins of a plurality of groups of pins extending from a surface of the receptacle connector (704). Controller 614 may activate at least one pin in a second group of pins of a plurality of groups of pins extending from the surface of the receptacle connector (706). A first interlocking wall of the first group of pins being separated from a second interlocking wall of the second group of pins by a creepage distance greater than a respective creepage distance threshold and a clearance distance greater than a respective clearance distance threshold.

In some examples, controller 614 may also activate at least one pin in a third group of pins of the plurality of groups of pins extending from the surface of the receptacle connector. The first interlocking wall of the first group of pins and the second interlocking wall of the second group of pins being separated from a third interlocking wall of the third group of pins by a creepage distance greater than the respective creepage distance threshold and clearance distance greater than the respective clearance distance threshold.

In some examples, controller 614 may also activate at least one pin in a fourth group of pins of the plurality of groups of pins extending from the surface of the receptacle connector. The first interlocking wall of the first group of pins, the second interlocking wall of the second group of pins, and the third interlocking wall of the third group of pins being separated from a fourth interlocking wall of the fourth group of pins by a creepage distance greater than the respective creepage distance threshold and clearance distance greater than the respective clearance distance threshold.

In some examples, controller 614 may also activate at least one pin in a fifth group of pins of the plurality of groups of pins extending from the surface of the receptacle connector. The first interlocking wall of the first group of pins, the second interlocking wall of the second group of pins, the third interlocking wall of the third group of pins, and the fourth interlocking wall of the fourth group of pins being separated from a fifth interlocking wall of the fifth group of pins by a creepage distance greater than the respective creepage distance threshold and clearance distance greater than the respective clearance distance threshold In some examples, controller 614 may transfer electrical energy from each pin of the respective first group to a first group of electrodes of the plurality of electrodes. Controller 614 may transfer electrical energy from each pin of the respective second group to a second group of electrodes of the plurality of electrodes, the second group of electrodes being different than the first group of electrodes.

In some examples, controller 614 may drive the activated pin(s) of the first group to a negative polarity and drive the activated pin(s) of the second group to a positive polarity. In some examples, controller 614 may activate only one pin in a respective group of pins at a time while performing PFA.

In some examples, each of the pins in a respective group of pins may be electrically isolated from each of the pins in a different group of pins. In some examples, each of the plurality of groups of pins include at least two pins.

The techniques described in this disclosure may be implemented, at least in part, in hardware, software, firmware or any combination thereof. For example, various aspects of the described techniques may be implemented within processing circuitry, which may include one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also form one or more processors or processing circuitry configured to perform one or more of the techniques of this disclosure.

Such hardware, software, and firmware may be implemented, and various operation may be performed within same device, within separate devices, and/or on a coordinated basis within, among or across several devices, to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components. Processing circuitry described in this disclosure, including a processor or multiple processors, may be implemented, in various examples, as fixed-function circuits, programmable circuits, or a combination thereof.

Fixed-function circuits refer to circuits that provide particular functionality with preset operations. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive stimulation parameters or output stimulation parameters), but the types of operations that the fixed-function circuits perform are generally immutable. In some examples, one or more of the units may be distinct circuit blocks (fixed-function or programmable), and in some examples, one or more of the units may be integrated circuits.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media. It should also be understood that when describing electrodes as being anodes or cathodes, this is not intended to imply that direct current is being delivered but in general, this disclosure uses such terms to denote that electrodes which are called anodes are connected to the opposite polarity of those called cathodes when delivering alternating current or most commonly, biphasic pulsed waveforms. Such biphasic waveforms may be delivered as a series of pulses (pulse train) that consists of a positive square wave pulse followed by a negative square wave pulse where such a pulse train may consist of tens or hundreds of such alternating polarity (biphasic) pulses.

The following examples are illustrative of the techniques described herein.

Example 1: A receptacle connector for a catheter for performing pulsed field ablation (PFA), the receptacle connector includes a first side to receive electrical signals; a second side, opposite to the first side, to transfer the electrical signals to a plurality of electrodes; a surface on the first side; and a plurality of groups of pins extending from the surface, each group of the plurality of groups of pins including: at least one pin configured to electrically connect to a power source to receive the electrical signals, and an interlocking wall surrounding the at least one pin.

Example 2: The receptacle connector of example 1, wherein each of the plurality of groups of pins include at least two pins.

Example 3: The receptacle connector of any of examples 1 and 2, wherein the plurality of groups of pins comprises: a first group including a plurality of first pins; a second group including a plurality of second pins; a third group including a plurality of third pins; a fourth group including a plurality of fourth pins; and a fifth group including a plurality of fifth pins.

Example 4: The receptacle connector of any of examples 1 through 3, wherein the interlocking wall of at least one of the groups is shaped as a discorectangle.

Example 5: The receptacle connector of any of examples 1 through 4, wherein a space separates each group of pins from the other groups of pins.

Example 6: The receptacle connector of any of examples 1 through 5, wherein a creepage distance separates each group of pins from the other groups of pins, the creepage distance being greater than a creepage distance threshold.

Example 7: The receptacle connector of any of examples 1 through 6 wherein a clearance distance separates each group of pins from the other groups of pins, the clearance distance being greater than a clearance distance threshold.

Example 8: The receptacle connector of example 7, wherein the clearance distance threshold corresponds to a clearance requirement of 1500 volt therapy.

Example 9: The receptacle connector of any of examples 6 through 8, wherein the creepage distance threshold corresponds to a creepage requirement of 1500 volt therapy.

Example 10: The receptacle connector of any of examples 1 through 9, wherein each of the pins in a respective group of pins is electrically isolated from each of the pins in a different group of pins.

Example 11: The receptacle connector of any of examples 1 through 10, wherein each pin in a respective group of pins is configured to transfer electrical energy to the same respective electrodes of the plurality of electrodes.

Example 12: The receptacle connector of any of examples 1 through 11, wherein each group of the plurality of groups of pins is configured to transfer electrical energy to different respective electrodes of the plurality of electrodes than the other respective groups of pins.

Example 13: The receptacle connector of any of examples 1 through 12, wherein the receptacle connector is located at least partially inside a handle of the catheter.

Example 14: A method for performing pulsed field ablation (PFA) includes determining, by a controller connected to a catheter and at a first time, to perform PFA; responsive to determining to perform PFA, outputting, by the controller and through a receptacle connector to a plurality of electrodes of the catheter to cause the plurality of electrodes to generate a field, electrical energy to activate at least one pin in a first group of pins of a plurality of groups of pins extending from a surface of the receptacle connector.

Example 15: The method of example 14, wherein outputting electrical energy through the receptacle connector to cause the plurality of electrodes to generate the field comprises: activating at least one pin in a second group of pins of the plurality of groups of pins extending from the surface of the receptacle connector, a first interlocking wall of the first group of pins being separated from a second interlocking wall of the second group of pins by a creepage distance greater than a respective creepage distance threshold and a clearance distance greater than a respective clearance distance threshold.

Example 16: The method of example 15, wherein the creepage distance threshold corresponds to a creepage requirement of 1500 volt therapy and the clearance distance threshold corresponds to a clearance requirement of 1500 volt therapy.

Example 17: The method of any of examples 15 through 16, wherein outputting electrical energy through the receptacle connector to cause the plurality of electrodes to generate the field comprises: activating at least one pin in a third group of pins of the plurality of groups of pins extending from the surface of the receptacle connector, the first interlocking wall of the first group of pins and the second interlocking wall of the second group of pins being separated from a third interlocking wall of the third group of pins by a creepage distance greater than the respective creepage distance threshold and clearance distance greater than the respective clearance distance threshold.

Example 18: The method of example 17, wherein outputting electrical energy through the receptacle connector to cause the plurality of electrodes to generate the field comprises: activating at least one pin in a fourth group of pins of the plurality of groups of pins extending from the surface of the receptacle connector, the first interlocking wall of the first group of pins, the second interlocking wall of the second group of pins, and the third interlocking wall of the third group of pins being separated from a fourth interlocking wall of the fourth group of pins by a creepage distance greater than the respective creepage distance threshold and clearance distance greater than the respective clearance distance threshold.

Example 19: The method of example 18, wherein outputting electrical energy through the receptacle connector to cause the plurality of electrodes to generate the field comprises: activating at least one pin in a fifth group of pins of the plurality of groups of pins extending from the surface of the receptacle connector, the first interlocking wall of the first group of pins, the second interlocking wall of the second group of pins, the third interlocking wall of the third group of pins, and the fourth interlocking wall of the fourth group of pins being separated from a fifth interlocking wall of the fifth group of pins by a creepage distance greater than the respective creepage distance threshold and clearance distance greater than the respective clearance distance threshold.

Example 20: The method of any of examples 15 through 19, wherein outputting electrical energy through the receptacle connector to cause the plurality of electrodes to generate the field comprises: driving the activated pin of the first group to a negative polarity; and driving the activated pin of the second group to a positive polarity.

Example 21: The method of any of examples 15 through 20, wherein outputting electrical energy through the receptacle connector to cause the plurality of electrodes to generate the field comprises: activating only one pin in a respective group of pins at a time while performing PFA.

Example 22: The method of any of examples 15 through 21, wherein each of the pins in a respective group of pins is electrically isolated from each of the pins in a different group of pins.

Example 23: The method of any of examples 15 through 22, wherein each of the plurality of groups of pins include at least two pins.

Example 24: The method of any of examples 15 through 23, further includes transferring electrical energy from each pin of the respective first group to a first group of electrodes of the plurality of electrodes; and transferring electrical energy from each pin of the respective second group to a second group of electrodes of the plurality of electrodes, the second group of electrodes being different than the first group of electrodes.

Example 25: A system includes a catheter; and one or more processors configured to perform the method of claim 14.

Example 26: A non-transitory computer-readable storage medium storing instructions that, when executed, cause processing circuitry to perform the method of any of examples 14 through 25.

Various examples have been described. These and other examples are within the scope of the following claims.

What is claimed is:

1. A receptacle connector for a catheter for performing pulsed field ablation (PFA), the receptacle connector comprising:
   a first side to receive electrical signals, the first side defining a surface;
   a second side, opposite to the first side, to transfer the electrical signals to a plurality of electrodes; and
   a plurality of groups of pins extending from the surface, each group of the plurality of groups of pins including:
      at least one pin configured to electrically connect to a power source to receive an electrical signal of the electrical signals, and
      an interlocking wall extending from the surface and surrounding the at least one pin.

2. The receptacle connector of claim 1, wherein each of the plurality of groups of pins include at least two pins.

3. The receptacle connector of claim 1, wherein the plurality of groups of pins comprises:
   a first group including a plurality of first pins;
   a second group including a plurality of second pins;
   a third group including a plurality of third pins;
   a fourth group including a plurality of fourth pins; and
   a fifth group including a plurality of fifth pins.

4. The receptacle connector of claim 1, wherein the interlocking wall of at least one of the groups is shaped as a discorectangle.

5. The receptacle connector of claim 1, wherein a space separates each group of pins from the other groups of pins.

6. The receptacle connector of claim 1, wherein a creepage distance separates each group of pins from the other groups of pins, the creepage distance being greater than a creepage distance threshold.

7. The receptacle connector of claim 1, wherein a clearance distance separates each group of pins from the other groups of pins, the clearance distance being greater than a clearance distance threshold.

8. The receptacle connector of claim 7, wherein the clearance distance threshold corresponds to a clearance requirement of 1500 volt therapy.

9. The receptacle connector of claim 6, wherein the creepage distance threshold corresponds to a creepage requirement of 1500 volt therapy.

10. The receptacle connector of claim 1, wherein each of the pins in a respective group of pins is electrically isolated from each of the pins in a different group of pins.

11. The receptacle connector of claim 1, wherein each pin in a respective group of pins is configured to transfer electrical energy to the same respective electrodes of the plurality of electrodes.

12. The receptacle connector of claim 1, wherein each group of the plurality of groups of pins is configured to transfer electrical energy to different respective electrodes of the plurality of electrodes than the other respective groups of pins.

13. The receptacle connector of claim 1, wherein the receptacle connector is located at least partially inside a handle of the catheter.

14. A method for performing pulsed field ablation (PFA), the method comprising:
   determining, by a controller connected to a catheter and at a first time, to perform PFA; and
   responsive to determining to perform PFA, outputting, by the controller and through a receptacle connector to a plurality of electrodes of the catheter to cause the plurality of electrodes to generate a field, electrical energy to activate at least one pin in a first group of pins of a plurality of groups of pins extending from a surface of the receptacle connector, a first interlocking wall extending from the surface and surrounding the first group of pins.

15. The method of claim 14, wherein outputting electrical energy through the receptacle connector to cause the plurality of electrodes to generate the field comprises:
    activating at least one pin in a second group of pins of the plurality of groups of pins extending from the surface of the receptacle connector, the first interlocking wall of the first group of pins being separated from a second interlocking wall extending from the surface and surrounding the second group of pins by a creepage distance greater than a respective creepage distance threshold and a clearance distance greater than a respective clearance distance threshold.

16. The method of claim 15, wherein outputting electrical energy through the receptacle connector to cause the plurality of electrodes to generate the field comprises:
    activating at least one pin in a third group of pins of the plurality of groups of pins extending from the surface of the receptacle connector, the first interlocking wall of the first group of pins and the second interlocking wall of the second group of pins being separated from a third interlocking wall extending from the surface and surrounding the third group of pins by a creepage distance greater than the respective creepage distance threshold and clearance distance greater than the respective clearance distance threshold.

17. The method of claim 16, wherein outputting electrical energy through the receptacle connector to cause the plurality of electrodes to generate the field comprises:
    activating at least one pin in a fourth group of pins of the plurality of groups of pins extending from the surface of the receptacle connector, the first interlocking wall of the first group of pins, the second interlocking wall of the second group of pins, and the third interlocking wall of the third group of pins being separated from a fourth interlocking wall extending from the surface and surrounding the fourth group of pins by a creepage distance greater than the respective creepage distance threshold and clearance distance greater than the respective clearance distance threshold.

18. The method of claim 17, wherein outputting electrical energy through the receptacle connector to cause the plurality of electrodes to generate the field comprises:
    activating at least one pin in a fifth group of pins of the plurality of groups of pins extending from the surface of the receptacle connector, the first interlocking wall of the first group of pins, the second interlocking wall of the second group of pins, the third interlocking wall of the third group of pins, and the fourth interlocking wall of the fourth group of pins being separated from a fifth interlocking wall extending from the surface and surrounding the fifth group of pins by a creepage distance greater than the respective creepage distance threshold and clearance distance greater than the respective clearance distance threshold.

19. The method of claim 15, wherein outputting electrical energy through the receptacle connector to cause the plurality of electrodes to generate the field comprises:
    driving the activated pin of the first group to a negative polarity; and
    driving the activated pin of the second group to a positive polarity.

20. The method of claim 14, wherein outputting electrical energy through the receptacle connector to cause the plurality of electrodes to generate the field comprises:
    activating only one pin in a respective group of pins at a time while performing PFA.

21. The method of claim 15, further comprising:
    transferring electrical energy from each pin of the respective first group to a first group of electrodes of the plurality of electrodes; and
    transferring electrical energy from each pin of the respective second group to a second group of electrodes of the plurality of electrodes, the second group of electrodes being different than the first group of electrodes.

* * * * *